(12) United States Patent
Jensen et al.

(10) Patent No.: US 7,473,696 B2
(45) Date of Patent: *Jan. 6, 2009

(54) CCR-2 ANTAGONIST SALT

(75) Inventors: Mark Jensen, Holmdel, NJ (US); Robert Larsen, Bridgewater, NJ (US); Daniel Richard Sidler, Whitehouse Station, NJ (US)

(73) Assignee: Merck & Co., Inc., Rahway, NJ (US)

( * ) Notice: Subject to any disclaimer, the term of this patent is extended or adjusted under 35 U.S.C. 154(b) by 103 days.

This patent is subject to a terminal disclaimer.

(21) Appl. No.: 10/577,584

(22) PCT Filed: Oct. 25, 2004

(86) PCT No.: PCT/US2004/035069

§ 371 (c)(1),
(2), (4) Date: Apr. 27, 2006

(87) PCT Pub. No.: WO2005/044264

PCT Pub. Date: May 19, 2005

(65) Prior Publication Data

US 2007/0135474 A1    Jun. 14, 2007

Related U.S. Application Data

(60) Provisional application No. 60/514,735, filed on Oct. 27, 2003.

(51) Int. Cl.
*A61K 31/4375* (2006.01)
*C07D 471/04* (2006.01)

(52) U.S. Cl. .................................... 514/300; 546/122
(58) Field of Classification Search ................ 514/300; 546/122
See application file for complete search history.

(56) References Cited

U.S. PATENT DOCUMENTS 6,812,234 B2 * 11/2004 Jiao et al. .................... 514/300

FOREIGN PATENT DOCUMENTS

WO    WO 03/093266 A1    11/2003

* cited by examiner

*Primary Examiner*—Charanjit S Aulakh
(74) *Attorney, Agent, or Firm*—James L. McGinnis; Mark R. Daniel

(57) ABSTRACT

An efficient synthesis for the preparation of ((1R,3S)-3-isopropyl-3-{[3-(trifluoromethyl)-7,8-dihydro-1,6-naphthyridin-6(5H)-yl]carbonyl} cyclopentyl)[(3S,4S)-3-methoxytetrahydro-2H-pyran-4-yl]amine and its succinate salt are provided. The succinate salt is crystalline and has superior properties.

2 Claims, No Drawings

CCR-2 ANTAGONIST SALT

RELATED APPLICATION DATA

This is a National filing under 35 USC 371 of PCT/US2004/035069, filed Oct. 25, 2004, which claims priority from U.S. Ser. No. 60/514,735, filed Oct. 27, 2003.

BACKGROUND OF THE INVENTION

International patent applications US03/12929, filed Apr. 25, 2003, and US03/13042, filed Apr. 25, 2003, disclose tetrahydropyranyl cyclopentyl tetrahydropyridopyridine compounds. These compounds are useful for the treatment of diseases or conditions of humans or other species which can be treated with inhibitors, modulators or promoters of chemokine receptor function. Such diseases or conditions include those mentioned in the referenced applications.

((1R,3S)-3-Isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine, 1:

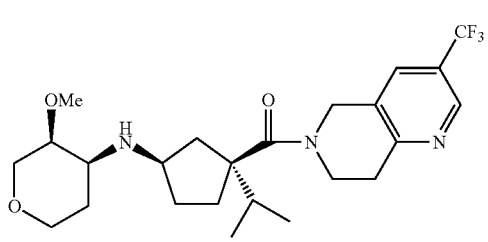

is a potent CCR-2 inhibitor. The laboratory preparation of compound 1, including the laboratory preparation of certain intermediates and precursors employed to in the synthesis of compound 1 is described in International patent application US03/12929 and US03/13042.

Prior techniques for synthesizing compound 1 were inefficient and time consuming, and thus expensive from the standpoint of production. The synthesis of the naphthyridine building block, for example, comprised nine separate steps and required the use of several expensive reagents, hampering the efficiency of the overall synthetic process. Similarly, the synthesis of the cyclopentene building block resulted in a high proportion of undesirable stereoisomers. Other aspects of the synthesis were likewise inefficient, expensive, and/or not amenable to commercial production. Previously synthesized hydrochloride salts of compound 1, moreover, displayed less than ideal solubility, handling (e.g., hydroscopicity) and other properties. Thus, there remains a need for an improved synthetic route to compound 1 that is amenable to large scale production formulation, storage and distribution. There also remains a need to develop improved salt forms of compound 1.

SUMMARY OF THE INVENTION

The present invention provides an efficient synthesis for the preparation of ((1R,3S)-3-isopropyl--{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine and its succinate salt. The present invention additionally provides an efficient syntheses for the preparation of intermediates (3R)-3-methoxytetrahydro-4H-pyran-4-one; (1S,4S)-4-(2,5-dimethyl-1H-pyrrol-1-yl)1-isopropyl-cyclopent-2-ene-1-carboxylic acid; and 3-(trifluoromethyl)-5,6,7,8-tetrahydro-1,6-naphthyridine; and for the preparation of the precursor (3S,4S)-N-((1S,4S)-4-isopropyl-4-{[3-(trifluoromethyl)-7,8-dihydro-1,6-naphthyridin-6(5H)-yl]carbonyl}cyclopent-2-en-1-yl)-3-methoxytetrahydro-2H-pyran-4-amine. The invention additionally resides in the superior properties of the succinate salt of ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine.

DETAILED DESCRIPTION OF THE INVENTION

In one aspect, the present invention provides a process for the preparation of (3S,4S)-N-((1S,4S)-4-isopropyl-4-{[3-(trifluoromethyl)-7,8-dihydro-1,6-naphthyridin-6(5H)-yl]carbonyl}cyclopent-2-en-1-yl)-3-methoxytetrahydro-2H-pyran-4-amine, 2:

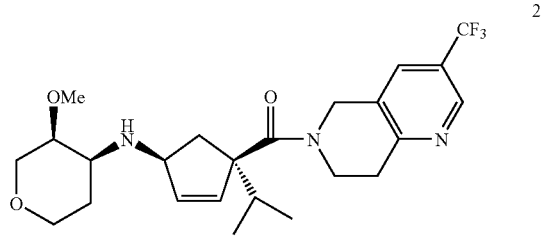

comprising the steps of:

(1) reacting (1S,4S)-4-(2,5-dimethyl-1H-pyrrol-1-yl)-1-isopropylcyclopent-2-ene-1-carboxylic acid with 3-(trifluoromethyl)-5,6,7,8-tetrahydro-1,6-naphthyridine to form 6-{[(1S,4S)-4-(2,5-dimethyl-1H-pyrrol-1-yl)-1-isopropylcyclopent-2-en-1-yl]carbonyl}-3-(trifluoromethyl)-5,6,7,8-tetrahydro-1,6-naphthyridine;

(2) treating the 6-{[(1S,4S)-4-(2,5-dimethyl-1H-pyrrol-1-yl)-1-isopropylcyclopent-2-en-1-yl]carbonyl}-3-(trifluoromethyl)-5,6,7,8-tetrahydro-1,6-naphthyridine with hydroxylamine to form (1S,4S)-4-isopropyl-4-{[3-(trifluoromethyl)-7,8-dihydro-1,6-naphthyridin-6(5H)-yl]carbonyl}cyclopent-2-en-1-amine; and (3) coupling the (1S,4S)-4-isopropyl-4-{[3-(trifluoromethyl)-7,8-dihydro-1,6-naphthyridin-6(5H)-yl]carbonyl}cyclopent-2-en-1-amine with (3R)-3-methoxytetrahydro-4H-pyran-4-one via reductive amination.

In a further aspect, the present invention provides a process for the preparation of ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine, 1:

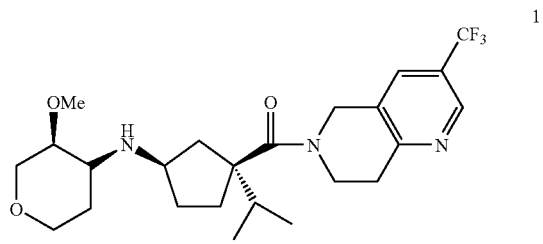

comprising the further step of:

(4) hydrogenating (3S,4S)-N-((1S,4S)-4-isopropyl-4-{[3-(trifluoromethyl)-7,8-dihydro-1,6-naphthyridin-6(5H)-yl]carbonyl}cyclopent-2-en-1-yl)-3-methoxytetrahydro-2H-pyran-4-amine.

In another aspect of the invention, discussed in greater detail below, the hydrogenation step is accomplished prior to the formation of compound 2.

The syntheses of (3S,4S)-N-((1S,4S)-4-isopropyl-4-{[3-(trifluoromethyl)-7,8-dihydro-1,6-naphthyridin-6(5H)-yl]carbonyl}cyclopent-2-en-1-yl)-3-methoxytetrahydro-2H-pyran-4-amine, 2, and ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine, 1, are depicted in Scheme 1:

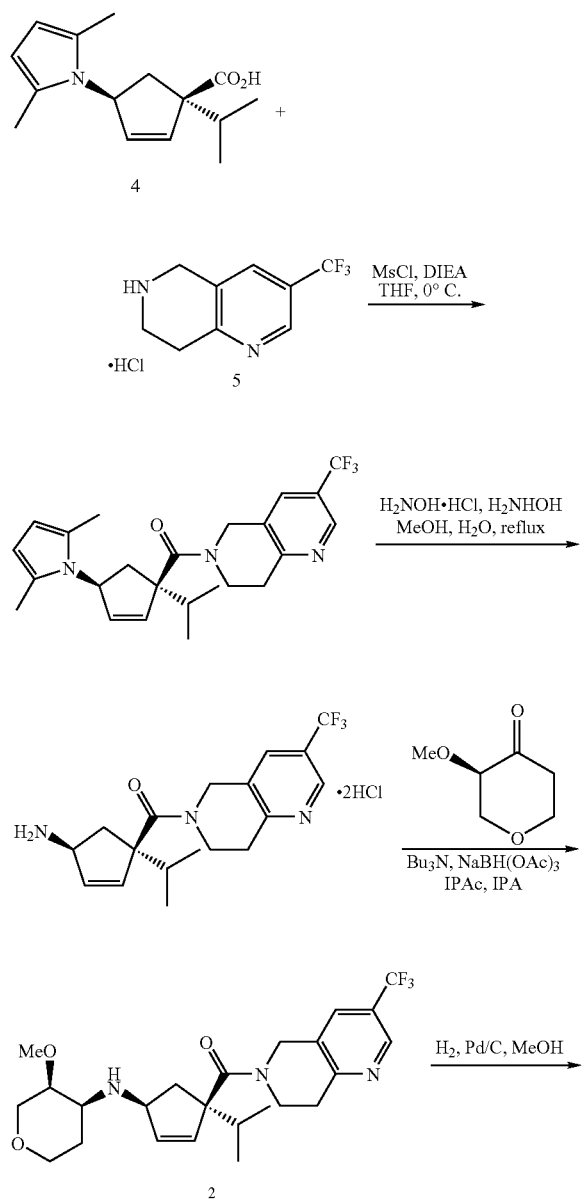

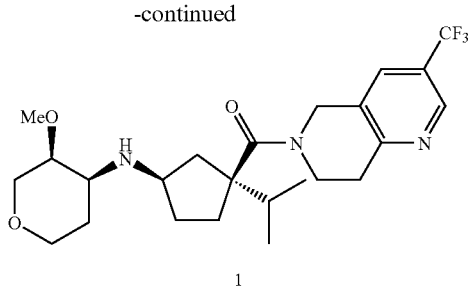

N-((1R,3S)-3-isopropyl-3-{[3-(trifluoromethyl)-7,8-dihydro-1,6-naphthyridin-6(5H)-yl]carbonyl}cyclopentyl)-N-[(cis-3S,4S)-3-methoxytetrahydro-2H-pyran-4-yl]amine, 1, is synthesized by sequentially coupling three building block compounds 4, 5 and 6 (Schemes 3, 4 and 5, below). An amidation reaction between 3-(trifluoromethyl)-5,6,7,8-tetrahydro-1,6-naphthyridine, 5, and (1S,4S)-4-(2,5-dimethyl-1H-pyrrol-1-yl)1-isopropylcyclopent-2-ene-1-carboxylic acid, 4, is carried out in the presence of methanesulfonyl chloride to afford 6-{[(1S,4S)-4-(2,5-dimethyl-1H-pyrrol-1-yl)-1-isopropylcyclopent-2-en-1-yl]carbonyl}-3-(trifluoromethyl)-5,6,7,8-tetrahydro-1,6-naphthyridine. Deprotection of the pyrrole group was carried out at this stage using hydroxylamine as a through process to provide an amine salt. The amine salt and (3R)-3-methoxytetrahydro-4H-pyran-4-one, 6, are coupled through reductive amination, in the presence of a tributylamine buffer, and with NaBH(OAc)₃ to afford (3S,4S)-N-((1S,4S)-4-isopropyl-4-{[3-(trifluoromethyl)-7,8-dihydro-1,6-naphthyridin-6(5H)-yl]carbonyl}cyclopent-2-en-1-yl)-3-methoxytetrahydro-2H-pyran-4-amine, 2. The cyclopentene moiety of compound 2 was then hydrogenated to form free base compound 1.

In another aspect the invention provides a process for the preparation of ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine succinate, 3:

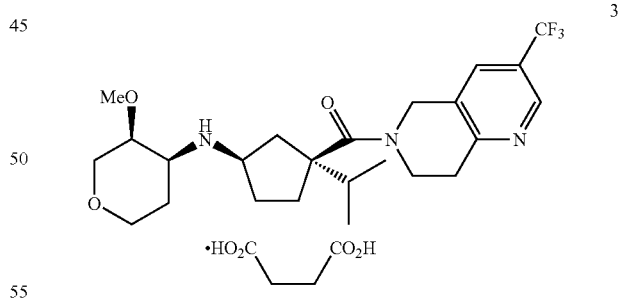

comprising the further step of:

(5) contacting ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine, 1, with succinic acid.

Optionally, prior to step (5) compound 1 may be purified employing crystallization, either as a succinate salt or other salt such as a benzenesulfonate salt, followed by a salt break. Purification in this manner is described in the examples which follow.

The synthesis of compound 3, the succinate salt, is depicted in Scheme 2:

Scheme 2

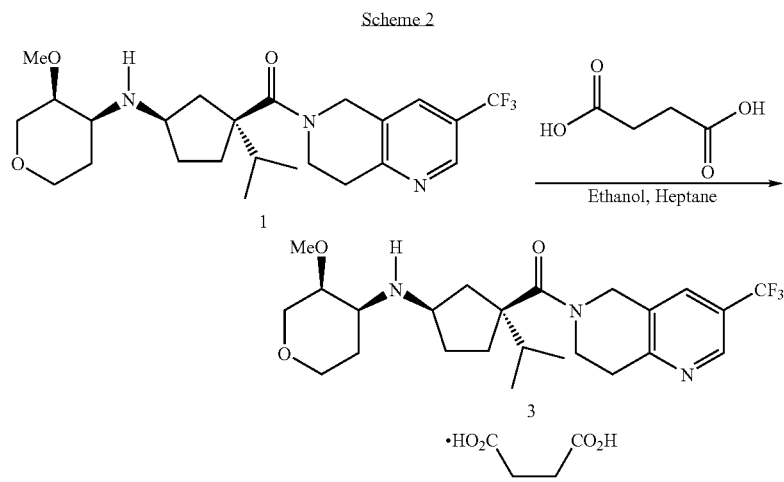

In another aspect, the invention provides a process for the preparation of the intermediate (1S,4S)-4-(2,5-dimethyl-1H-pyrrol-1-yl)-1-isopropylcyclopent-2-ene-1-carboxylic acid, 4, comprising the steps of:

(1) reacting (1R,4S)-4-aminocyclopenten-2-ene-1-carboxylic acid with MeOH in the presence thionyl chloride to form methyl (1R,4S)-4-aminocyclopent-2-ene-1-carboxylate;

(2) reacting said methyl (1R,4S)-4-aminocyclopent-2-ene-1-carboxylate with acetylacetone to form methyl (1R,4S)-4-(2,5-dimethyl-1H-pyrrol-1-yl)cyclopent-2-ene-1-carboxylate;

(3) reacting said methyl (1R,4S)-4-(2,5-dimethyl-1H-pyrrol-1-yl)cyclopent-2-ene-1-carboxylate with 2-iodopropane to form methyl (1S,4S)-4-(2,5-dimethyl-1H-pyrrol-1-yl)-1-isopropylcyclopent-2-ene-1-carboxylate; and (4) reacting said methyl (1S,4S)-4-(2,5-dimethyl-1H-pyrrol-1-yl)-1-isopropylcyclopent-2-ene-1-carboxylate with NaOH and MeOH to form (1S,4S)-4-(2,5-dimethyl-1H-pyrrol-1-yl)-1-isopropylcyclopent-2-ene-1-carboxylic acid.

The syntheses of (1S,4S)-4-(2,5-dimethyl-1H-pyrrol-1-yl)-1-isopropylcyclopent-2-ene-1-carboxylic acid, 4, is depicted in Scheme 3:

Scheme 3

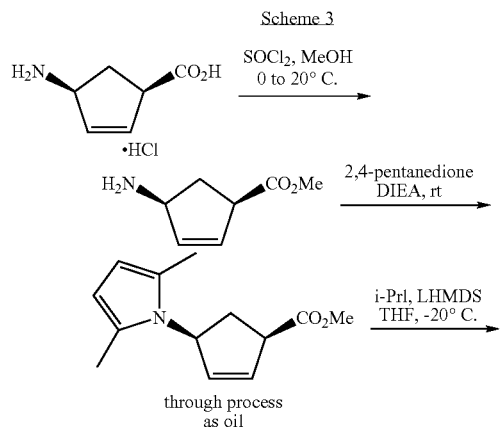

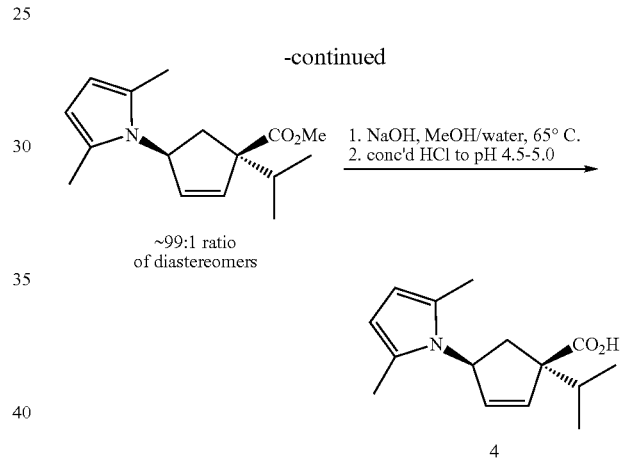

Here, (1R,4S)-4-aminocyclopent-2-ene-1-carboxylic acid is converted into the corresponding methyl ester by treatment with thionyl chloride in methanol. Methyl (1R,4S)-4-(2,5-dimethyl-1H-pyrrol-1-yl)cyclopent-2-ene-1-carboxylate is then synthesized by reacting the (1R,4S)-4-aminocyclopent-2-ene-1-carboxylate methyl ester with 2,4-pentanedione in the presence of DIEA. The following alkylation of methyl (1R,4S)-4-(2,5-dimethyl-1H-pyrrol-1-yl)cyclopent-2-ene-1-carboxylate with iodopropane is carried out using lithium bis-(trimethylsilyl)amide as a base. The resulting alkylated product is then hydrolyzed to form the (1S,4S)-4-(2,5-dimethyl-1H-pyrrol-1-yl)-1-isopropylcyclopent-2-ene-1-carboxylic acid 4.

While the above discussion assumes that the cyclopentene moiety will be hydrogenated in a later step to afford the cyclopentane, in fact many of the compounds depicted in Scheme 1 and 3 may be hydrogenated in an intervening step to produce a cyclopentane analog. (Because a pyrrole protecting group, if present, would also be reduced to a pyrrolidine during this process, an alternate protecting group could be employed.)

Moreover, in another feature of this aspect of the invention, intermediates may be synthesized having protecting groups other than 2,5-dimethyl-1H-pyrrol-1-yl. Thus, skilled chemists would pursue intermediate compounds of the general formula:

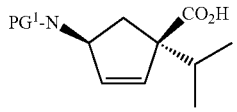

wherein the protecting group "PG$^1$" includes but is not limited to tert-butoxycarbonyl, benzyloxycarbonyl, alkyloxycarbonyl, allyloxycarbonyl, benzoyl, formyl, acetyl, trifluoroacetyl, 2-nitrobenzenesulfonyl, 4-nitrobenzenesulfonyl, 2,4-dinitrobenzenesulfonyl, benzyl, triphenylmethyl, imines (such as diphenylmethylene) and other protecting groups known in the art, as exemplified in Greene, T; Wuts, P. G. M. *Protective Groups in Organic Synthesis*, 3rd Ed., John Wiley & Sons, Inc., New York, N.Y. 1999.

In another aspect the invention provides a process for the preparation of the intermediate 3-(trifluoromethyl)-5,6,7,8-tetrahydro-1,6-naphthyridine, 5, comprising the steps of:

(1) reacting 3,3,3-trifluoropropanoic acid with POCl$_3$, DMF, NaPF$_6$ and a base to form N-[3-(dimethylamino)-2-(trifluoromethyl)prop-2-enylidene]-N-methylmethanamium hexafluorophosphate (CF$_3$DT);

(2) reacting CF$_3$DT with the protected piperidone to form—N-(protecting group)-3-(trifluoromethyl)-5,6,7,8-tetrahydro-1,6-naphthyridine (for example, reacting CF$_3$DT with BOC-piperidone to form —N-(tert-butoxycarbonyl)-3-(trifluoromethyl)-5,6,7,8-tetrahydro-1,6-naphthyridine); and (3) reacting said—N-(protecting group)-3-(trifluoromethyl)-5,6,7,8-tetrahydro-1,6-naphthyridinene (for example, N-(tert-butoxycarbonyl)-3-(trifluoromethyl)-5,6,7,8-tetrahydro-1,6-naphthyridine) in the presence of HCl and methanol to form—3-(trifluoromethyl)-5,6,7,8-tetrahydro-1,6-naphthyridine.

The syntheses of 3-(trifluoromethyl)-5,6,7,8-tetrahydro-1,6-naphthyridine, 5, is depicted in Scheme 4A and 4B, below:

Scheme 4A

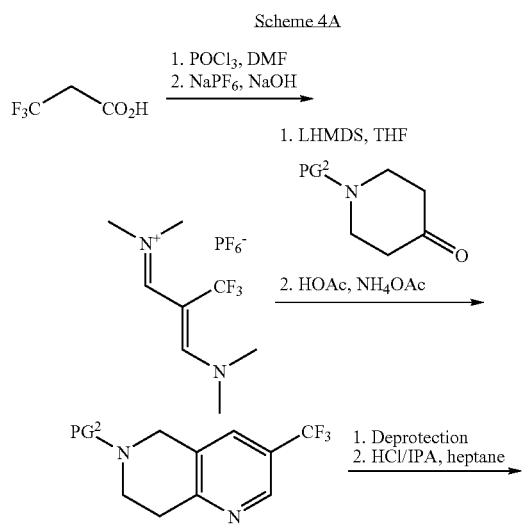

Scheme 4B

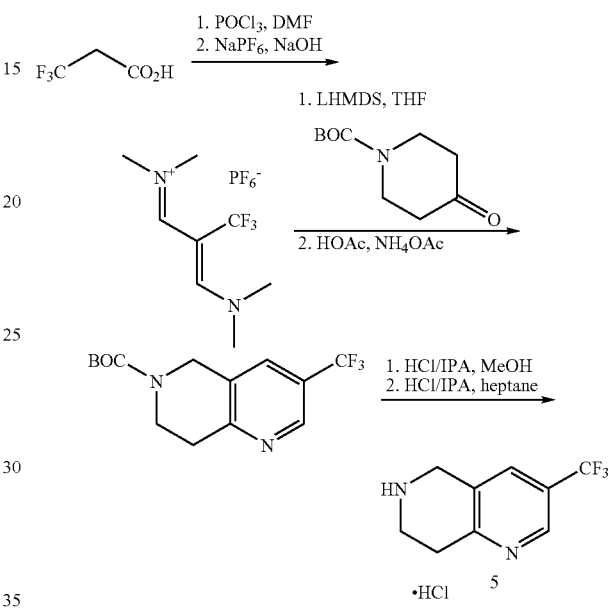

Phosphorous oxychloride (POCl$_3$) is added to chilled DMF at a rate such that the temperature remained below 10° C. (approx. 1 h). The reaction mixture is warmed to RT and then 3,3,3-trifluoropropanoic acid is added (exotherm to approx. 45° C.). The reaction mixture is warmed to 50° C. and held at this temperature for approx 4 h. Upon completion of the vinamidinium formation the reaction mixture is allowed to cool to RT. The reaction mixture is then added concurrently with 5 N NaOH to a solution of NaPF$_6$ in water cooled to 0° C. The rates of addition of the two solutions are controlled such that the temperature of the aqueous slurry remains below 10° C. and the pH is between 3 and 4 (addition time takes about 2 h). Upon completion of the additions the resulting yellow slurry is aged for one hour at 0° C. then filtered to collect solids. The filtercake is slurry washed with ice cold water (2 times) and the cake dried with nitrogen/vacuum. Typical yield 85%.

A solution of the protected piperidone, for instance the BOC protected piperidone, in THF is then added to a cooled (−20° C.) solution of lithium hexamethyldisilylamide (LiN(TMS)$_2$) in THF, keeping the temperature below 10° C., to form the lithium enolate (approx 45 min). After warming to RT the enolate solution is transferred to a chilled (−20° C.) slurry of the CF$_3$DT in THF at a rate such that the internal temperature remains below −10° C. (approx 45 min). This mixture is aged for 2 h at −20° C. then acetic acid is added and the mixture warmed to room temperature over 30 minutes. Ammonium acetate is then added and the mixture heated to 65° C. After two hours at 65° C. the reaction mixture is cooled to RT. Water and heptane are then added and the layers separated. The organic layer is washed with 2 M aqueous citric acid and then assayed for the BOC naphthyridine. Typical yield 65%.

Next, the organic layer from the naphthyridine formation is concentrated and solvent switched to methanol. HCl in IPA is then added and the mixture heated at 60° C. until the deprotection is complete (about 1 h). After cooling to room temperature water is added and the pH adjusted to appox 10.5. IPAc is added and the layers separated. The aqueous layer is back extracted with IPAc two additional times. The combined organic layers are concentrated and solvent switched to IPA. This IPA solution is filtered to remove inorganic salts, the filtercake washed with IPA and the combined filtrate and washes reconcentrated to a total volume of about 5 mL/g. After the free base/IPA solution to 60° C. HCl in IPA is added over 30 minutes. Solids are evident at about 50% addition. After completion of the HCl/IPA addition heptane is added to complete the crystallization and the slurry cooled to room temperature. The solids are isolated by filtration and washed with IPA/heptane (3 times 1 mL/g) then dried. Typical yield 75% from BOC naphthyridine.

As noted above, piperidones having protecting groups ("PG$^2$") other than tert-butoxycarbonyl may also be used. Other protecting groups useful in the synthesis of the naphthiridine include, but are not limited to benzyloxycarbonyl, alkyloxycarbonyl, allyloxycarbonyl, benzoyl, acetyl, formyl, trifluoroacetyl, 2-nitrobenzenesulfonyl, 4-nitrobenzenesulfonyl, 2,4-dinitrobenzenesulfonyl, N-benzyl, triphenylmethyl, and other protecting groups known in the art, as exemplified in Greene, T; Wuts, P. G. M. *Protective Groups in Organic Synthesis, 3rd Ed.*, John Wiley & Sons, Inc., New York, N.Y. 1999.

In another aspect the invention provides a process for the preparation of the intermediate (3R)-3-methoxytetrahydro-4H-pyran-4-one, 6, comprising the steps of:

(1) reacting tetrahyro-4H-pyran-4-one with tripropylorthoformate and chlorobenzene to form 4-propoxytetrahydro-2H-pyran-ethene;

(2) reacting said 4-propoxytetrahydro-2H-pyran-ethene in the presence of acetone, water, hydroquinidine-1,4-phthalazinediyl diether (DHQD$_2$PHAI), potassium osmate dehydrate, and 4-methylmorpholine N-oxide monohydrate (NMO) to form 3,4-dihydroxytetrahydro-2H-pyran-4-sulfonic acid, sodium salt;

(3) reacting said 3,4-dihydroxytetrahydro-2H-pyran-4-sulfonic acid, sodium salt with methanol and trimethylorthoformate in the presence of an acid to form 4,4-dimethoxytetrahydro-2H-pyran-3-ol; and (4) reacting said 4,4-dimethoxytetrahydro-2H-pyran-3-ol in the presence of THF, NaOt-Bu, Me$_2$SO$_4$, and an acid to form (3R)-3-methoxytetrahydro-4H-pyran-4-one.

The syntheses of (3R)-3-methoxytetrahydro-4H-pyran-4-one, 6, is depicted in the Scheme 5:

Scheme 5

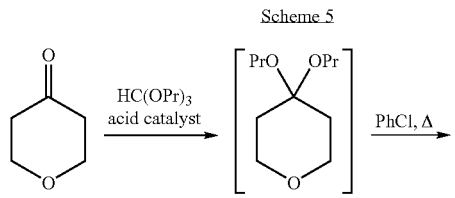

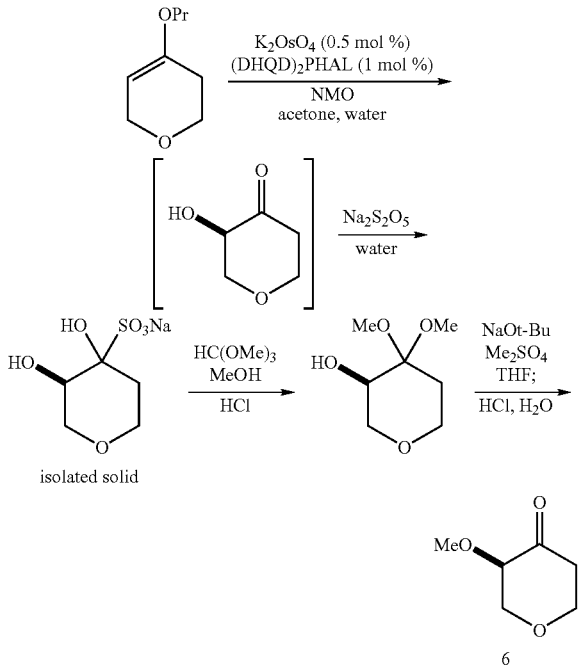

The starting pyranone is converted to its dipropyl ketal by treatment with tripropylorthoformate in the presence of an acid catalyst. The crude ketal is then heated in the presence of chlorobenzene. Under these conditions, elimination of propanol provides the propyl enol ether. The reaction is driven by the removal of propanol by distillation during the reaction sequence. The crude enol ether is then oxidized under modified Sharpless asymmetric dihydroxylation conditions. In this reaction N-methylmorpholine oxide is used as the stoichiometric oxidant. The reaction typically gives the product α-hydroxyketone in about 80 to 85% ee. The α-hydroxyketone is not isolated directly but an aqueous solution of Na$_2$S$_2$O$_5$ is added to form the bisulfite adduct of the ketone. From the acetone water mixture, racemic bisulfite adduct crystallizes. The racemate is removed by filtration and the resulting mother liquor is typically 95 to 99% enantiomeric excess (ee). The acetone is removed in vacuo and isopropanol is added to give the crystalline bisulfite adduct with high enantiomeric excess. This is treated with HCl and methanol with trimethylorthoformate as a water scavenger, to provide the dimethylketal. The hydroxyl group is then methylated using NaOt-Bu and Me$_2$SO$_4$. Adding water and HCl to the reaction mixture provides the target α-methoxypyranone in about 96% ee.

Several abbreviations, acronyms and other shorthand is presented herein. Although these terms are known to those skilled in the art, presented below is a table summarizing these terms:

| MSCl | methanesulfonyl chloride |
| --- | --- |
| DIEA | diisopropyl ethylamine |
| IPAc | isopropylacetate |
| IPA | ispropanol |
| i-PrI | 2-iodopropane |
| LHMDS | lithium hexamethyldisilazide |
| THF | tetrahydrofuran |
| DMF | dimethylformamide |

| P.G. | protecting group |
| --- | --- |
| BOC | tert-butyloxycarbonyl |
| NMO | N-methylmorphaline oxide |
| TFPA | Trifluoropropionic acid |

EXAMPLE 1

((1R,3S)-3-Isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine Step 1-6-{[(1S,4S)-4-(2,5-dimethyl-1H-pyrrol-1-yl)-1-isopropylcyclopent-2-en-1-yl]carbonyl}-3-(trifluoromethyl)-5,6,7,8-tetrahydro-1,6-naphthyridine

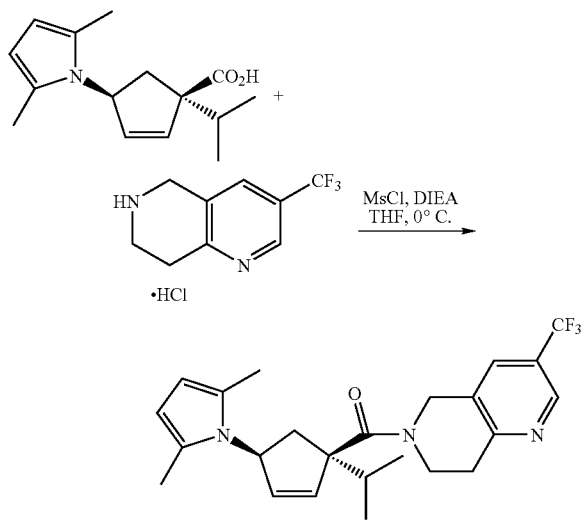

The pyrrole cyclopentene acid (730 g, 90.4 wt %, 2.67 mmol) and diisopropylethylamine (0.93 L, 5.34 mol) were mixed in THF (6.6 L). The resulting dark solution (KF=195 mg/mL) was cooled to 0° C., then methanesulfonyl chloride (228 mL, 2.94 mol) was added over 1 min whereupon the internal temperature increased to 13° C. over a few min. The cooling bath was removed and the mixture was aged at room temperature for 4 h. The reaction solution was cooled to ~15° C. and tetrahydronaphthyridine-HCl salt (670 g, 73.2 wt % as free base equivalent, 2.42 mol) was added. The temperature was increased to 23° C. and another portion of diisopropylethylamine (0.93 L, 5.34 mol) was added with cooling at ~25° C. over 15 min. The mixture was aged for >1 h and was then diluted with 5% NaHCO₃ (16 L). The product was extracted with ethyl acetate (EtOAc) (16 L). The organic phase was washed with water (10 L) and concentrated under vacuum with displacement of the EtOAc with methanol to a volume of 10 L. The assay yield of the amide was quantitative (1.055 kg, 2.45 mol).

Step 2—(1S,4S)-4-isopropyl-4-{[3-(trifluoromethyl)-7,8-dihydro-1,6-naphthyridin-6(5H)-yl]carbonyl}cyclopent-2-en-1-amine

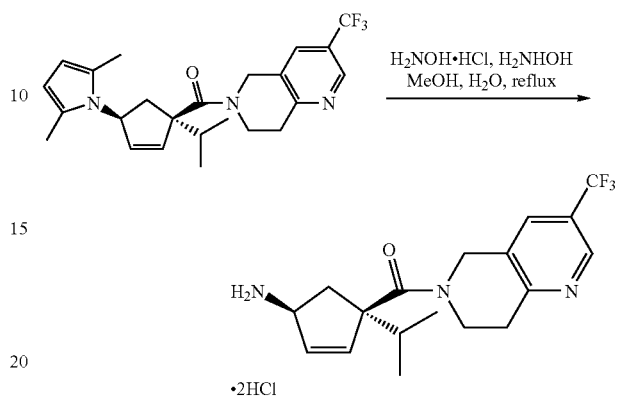

The amide (1.055 kg, 2.45 mol) in methanol (10 L) was added to hydroxylamine-HCl (1 kg, 14.4 mol), 50% hydroxylamine in water (1 L, 16.3 mol) and water (5 L). The resulting slurry was heated to reflux (71° C.) and maintained at this temperature for 6 h. The reaction solution was cooled to room temperature and the pH was adjusted to 11.0 with 10 N NaOH. The reaction solution was diluted with water (12 L) and the product was extracted with chlorobenzene three times (14 L, 13 L, and 13 L). Each organic layer was washed once with the same water (10 L). The organic layers containing product (0.79 assay kg, 2.24 mol, 92% yield) were combined and concentrated. The solvent was switched to isopropanol (8 L). Anhydrous HCl in IPA (4.3 N, 1.4 L, 6.0 mol) was added. This mixture was concentrated to ~2 L. The resulting slurry was heated to 70° C. and n-heptane (8 L) was added slowly. The slurry was cooled and aged at room temperature overnight (16 h). The solids were filtered, washed with of 20% IPA/heptane (1.5 L) and dried under nitrogen to yield 1.12 kg of the HCl salt (0.76 kg of free base equivalent) in 91% overall yield.

Step 3—(3S,4S)-N-((1S,4S)-4-isopropyl-4-{[3-(trifluoromethyl)-7,8-dihydro-1,6-naphthyridin-6(5H)-yl]carbonyl}cyclopent-2-en-1-yl)-3-methoxytetrahydro-2H-pyran-4-amine

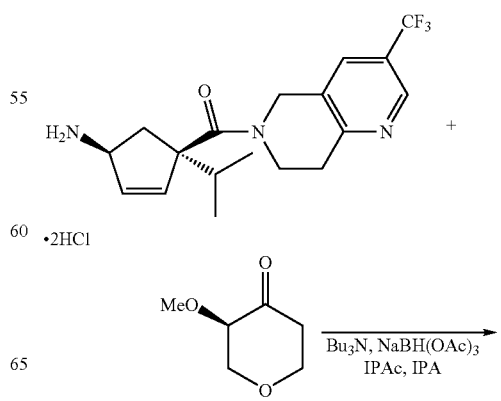

-continued

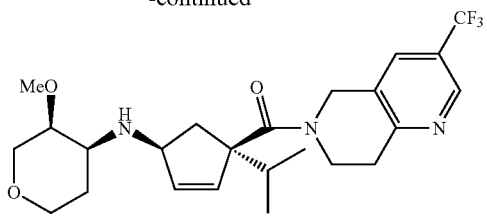

The amine dihydrochloride salt (777 g, 552 g as free base, 1.56 mol) was slurried in IPAc (3 L). The mixture was cooled in an ice bath and n-Bu$_3$N (860 mL, 3.61 mol) was added followed by isopropanol (260 mL, 3.40 mol). Sodium triacetoxyborohydride (724 g, 3.42 mol) was added at 5° C. After 1 h, a solution of the methoxypyranone in IPAc (1.76 L of a 160 g/L solution, 2.17 mol) was added to the batch at 1° C. After 6 h, the mixture was partitioned between saturated aq. NaHCO$_3$ (3 L), water (8 L), and EtOAc (10 L). The aqueous phase was further extracted with EtOAc (15 L). The combined organic phases were extracted with sat'd NaHCO$_3$ (4 L), dried over MgSO$_4$ (600 g), then concentrated. The resulting oil was dissolved in CH$_3$CN (15 L) and extracted with heptane (3×4 L). The acetonitrile phase contained 654 g (1.4 mol, 90%) (3S,4S)-N-((1S,4S)-4-isopropyl-4-{[3-(trifluoromethyl)-7,8-dihydro-1,6-naphthyridin-6(5H)-yl] carbonyl}cyclopent-2-en-1-yl)-3-methoxytetrahydro-2H-pyran-4-amine. The solvent was removed in vacuo to provide an oil that was used in the final hydrogenation step.

Step 4—((1R,3S)-3-Isopropyl-3-{[3-(trifluoromethyl)-7,8-dihydro-1,6-naphthyridin-6(5H)-yl] carbonyl}cyclopentyl)[(3S,4S)-3-methoxytetrahydro-2H-pyran-4-yl]amine

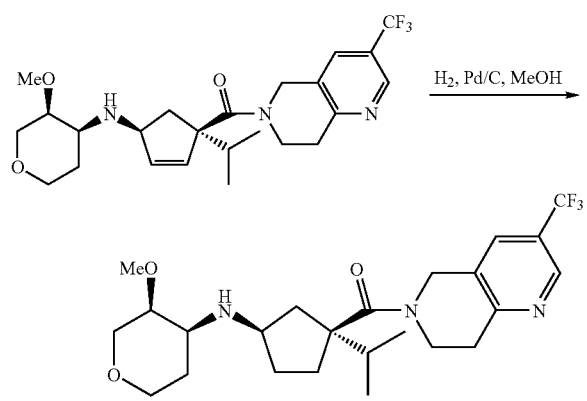

The crude coupled cyclopentene of Step 3 (640 g) was diluted with methanol (3.2 L) and the solution was concentrated to an oil. Dilution with methanol (3.2 L) and concentration were repeated two additional times. After the final concentration the oil was diluted with methanol (6.4 L) and charged to an autoclave. The catalyst 5% Pd/C (256 g) was charged to the autoclave as a slurry in methanol (1.4 L). The hydrogenation (40 psi) was run overnight (18 h) at 25° C. The batch was filtered through solka floc (~1.5 in depth) in an 8 L sintered-glass funnel. The autoclave was rinsed with methanol (5.0 L) and this rinse was used to wash the filter cake. The cake was washed again with methanol (1.3 L). The sequential rinsing was repeated four additional times. By LC assay the combined filtrate and washes (total wt=17.1 kg) contained 633 assay g (98.5% yield) of the free base. The filtrate and washes were concentrated to an oil (770 assay g, 1.634 mol). The oil was dissolved in IPA (3.1 L) and the solution was concentrated to a brown oil. Dilution with IPA (3.1 L) and concentration was repeated two additional times.

EXAMPLE 2

((1R,3S)-3-isopropyl-3-{[3-(trifluoromethyl)-7,8-dihydro-1,6-naphthyridin-6(5H)-yl] carbonyl}cylopentyl)[(3S,4S)-3-methoxytetrahydro-2H-pyran-4-yl]amine succinate Synthesis 1:

Purification from Benzenesulfonate Salt: The resulting oil from the Example 1 was dissolved in IPA (1.54 L) and transferred to crystallization flask. An IPA (2×385 mL) rinse was added to the batch. The solution was warmed to 56° C. at which point benzenesulfonic acid (283 g, 1.79 mol) was added which resulted in an increase in temperature to 71° C. The solution was cooled to 60° C. and benzenesulfonate salt seed (1 g) was added. The thin slurry was aged for 30 min to develop a thick seed bed after which heptane (4.62 L) was added over 50 min. After aging at 55 to 65° C. for 2 h the slurry was cooled to ambient temperature overnight. The slurry was filtered and the wet cake was washed with 2:1 heptane/IPA (2×2.3 L). The off-white solid was dried under N$_2$/vacuum to give the benzenesulfonate salt (875 g, 98.3 wt %) as a tan solid (84% adjusted yield). Water (11.1 L), IPAc (32 L), and ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine benzenesulfonate salt (1.645 kg) were added to a solution of K$_2$CO$_3$ (6.58 kg) in water (18.3 L). The mixture was aged 15 min. The layers were separated and the organic layer was washed with water (16 L). The IPAc solution of ((1R,3S)-3-Isopropyl-3-{[3-(trifluoromethyl)-7,8-dihydro-1,6-naphthyridin-6(5H)-yl] carbonyl}cyclopentyl)[(3S,4S)-3-methoxytetrahydro-2H-pyran-4-yl]amine free base (60.5 kg containing 1.16 kg free base) was concentrated to an oil. The resulting oil was diluted with ethanol (3.785 L) and reconcentrated to an oil. The dilution and concentration were repeated three more times.

Synthesis of the Succinic Acid Salt: After the final concentration the oil was diluted with ethanol (4.055 L). The ethanol solution was then heated to 65° C. Succinic acid (294 g, 2.48 mol) was added in one portion followed by addition of heptane (530 mL) over 10 min. The solution was then seeded with ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine succinate (5.8 g) as a slurry in heptane (50 mL). The resulting slurry was aged for 1 h at 65° C. during which time it noticeably thickened. At the end of the seed bed age, heptane (7.54 L) was added over 1.5 h. The slurry was aged for 2 h at 65° C., then allowed to cool to room temperature overnight (~9 h). The solids were filtered, washed with 2:1 heptane/ethanol (2×2.3 L, 2 mL/g free base), and dried under vacuum with a N$_2$ stream for 2 h. The filtercake was broken up and further dried with N$_2$/vacuum for ~48 h to afford 1.328 kg of the succinate salt (91.6%). The dried batch of ((1R,3S)-3-isopropyl-3-{[3-(trifluoromethyl)-7,8-dihydro-1,6-naphthyridin-6(5H)-yl] carbonyl}cyclopentyl)[(3S,4S)-3-methoxytetrahydro-2H-pyran-4-yl]amine succinate (1.328 g) was passed through a Comil using a 460 μm screen affording 1.313 g.

Synthesis 2

Formation of Succinate Salt: The free base (3034.2 g) was charged via a 1 μm inline filter to a 72 L flask equipped with a thermocouple, overhead stirrer, N₂/vacuum inlet, and batch concentrator, flask had been marked at 11.2 L. The combined concentrates were further concentrated to ~7 L and solvent switched to EtOH at constant volume using 17 L EtOH. The solution was diluted with EtOH to the 11.2 L mark on the flask. Vacuum was released and batch concentrator was replaced with an addition funnel. 839 g succinic acid was added and batch was warmed to 65° C. Heptane (1.4 L) was added over 7 min. 5 g seed was dissolved in 100 mL heptane and added to the batch. The thin slurry was aged 60 min to develop a thick seed bed after which 34.9 L heptane was added over 120 min. After aging at 65° C. for 2 h the slurry was cooled to ambient temp overnight. LC assay of the mother liquors showed a loss of 6.5 mg/mL. The slurry was filtered and wet cake slurry washed with 2×8 L 3/1 heptane/EtOH, followed by a 4 L displacement wash with 3/1 heptane/EtOH. The off white solid was dried under N²/vacuum on the filter pot to give 3404 g tan solid 96.7 wt %, 86% adjusted yield with 10.3% assay loss.

Recrystallization of Succinate Salt (Optional): 12.1 L EtOH was charged to a visually clean 50 L flask equipped with N²/vacuum inlet, mechanical stirrer, thermocouple, and inlet adaptor. Succinate salt was added and rinsed in with 4.7 L EtOH. Slurry was warmed to 65° C. at which point the solution was transferred to a 72 L flask under static vacuum via a 1 μm inline filter. When transfer was complete 50 L flask was rinsed with 1 L EtOH, rinse was transferred via inline filter to batch in 72 L flask. The filtered EtOH solution was concentrated at 38-44° C. with 25 in Hg to <12 L, succinate salt crystallized during the concentration. Slurry was diluted to 12.1 L then warmed to 65° C. 1 L Heptane was added followed by 14 g seed slurried in 300 mL heptane. Slurry was aged 1 h 10 min at 65° C. after which 17.5 L heptane was added over 2 h. The slurry was aged 2 h at 65° C. then cooled to room temp overnight, ~13 h. The slurry was filtered to collect the solids and the filtercake washed with 2:1 heptane:ethanol 5.4 L slurry wash, followed by 5.4 L displacement wash and 5.4 L slurry wash. The filtercake was dried by passing N₂ through it with vacuum for 3 h then the filtercake was broken up and further dried with N²/vacuum for approximately 48 h. After completion of drying the bulk drug was stored in a doubled polybag within a fiber drum to await milling. A total of 3.018 kg of the succinate salt (93.9% yield) was obtained.

EXAMPLE 3

(1S,4S)-4-(2,5-dimethyl-1H-pyrrol-1-yl)-1-isopropylcyclopent-2-ene-1-carboxylic acid Step 1—Methyl (1R,4S)-4-aminocyclopent-2-ene-1-carboxylate

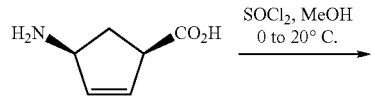

Solid (1R,4S)-4-aminocyclopenten-2-ene-1-carboxylic acid (1.0 kg, 7.72 mol) was dissolved in MeOH (3.0 L). The slurry was cooled to 0-5° C. Thionyl chloride (0.576 L, 7.92 mol) was added dropwise over 2 h maintaining a temperature <20° C. At the end of the thionyl chloride addition the cold bath was removed and the reaction mixture was aged at 20° C. for 1-2 h. The product mixture was then added dropwise to IPAc (22.5 L) over 1-2 h whereupon the product crystallized directly from solution as the HCl salt. The batch was filtered and dried in vacuo overnight to provide the aminocyclopentene methyl ester HCl salt (1081 g, 77% yield).

Step 2—Methyl(1R,4S)-4-(2,5-dimethyl-1H-pyrrol-1-yl)cyclopent-2-ene-1-carboxylate

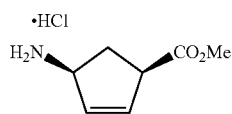

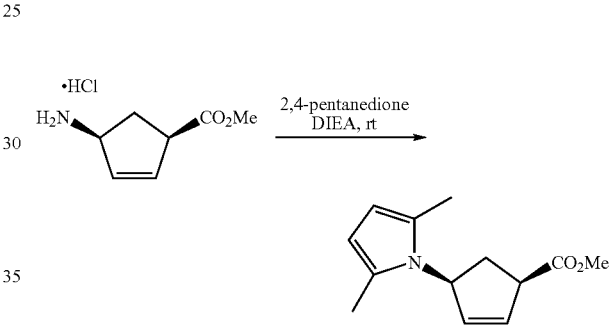

The solid aminocyclopentene methyl ester salt (1.076 kg, 6.059 mol) was dissolved in MeOH (3 L, 2M) at 20° C. under nitrogen. Diisopropylethylamine (DIEA, 0.78 kg, 6.059 mol) was added followed by acetonyl acetone (0.711 kg, 6.241 mol). The batch had an exotherm increasing the temperature to 32-35° C. The reaction mixture was then aged at 25° C. for 16 h. The batch was diluted with IPAc (9-10 L) and washed with 10% NH₄Cl (2×3 L) and 5% brine (2×3 L). The IPAc batch was dried over sodium sulfate, filtered, and concentrated to an oil. THF (3 L) was used as a flush and the batch was again concentrated to an oil. The air-sensitive pyrrole-protected aminocyclopentene carboxylate (1189 g, 92% yield) was stored at 5-7° C. under nitrogen until the alkylation step was run.

Step 3—Methyl (1S,4S)-4-(2,5-dimethyl-1H-pyrrol-1-yl)-1-isopropylcyclopent-2-ene-1-carboxylate

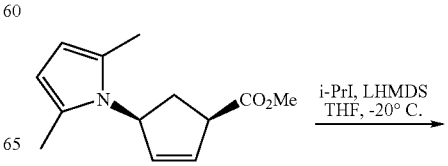

-continued

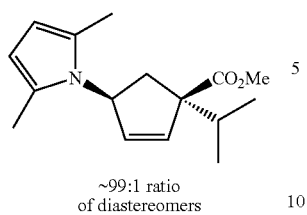

~99:1 ratio of diastereomers

The pyrrole methyl ester (1189 g) dissolved in THF (1.2 L) was added dropwise over 40 min to 1 M lithium hexamethyldisilazide (LHMDS) in THF (8.65 L, 8.650 mol) at −20° C. The batch was aged for 30 min and 2-iodopropane was added over 1 h. The batch was aged for 1 h, then allowed to warm to 20° C. over 2 h and aged at 20° C. for 1-2 h until complete by HPLC (<0.5% starting material). The batch was quenched into 6% NH$_4$Cl solution (10 L). IPAc (20 L) was charged and the layers were separated. The organic layer was washed with 6% aq NH$_4$Cl (10 L), 5% brine (2×10 L), and concentrated to an oil. The air-sensitive alkylated pyrrole methyl ester (1419 g, 98% yield) was stored at 5-7° C. under nitrogen until saponified.

Step 4—(1S,4S)-4-(2,5-dimethyl-1H-pyrrol-1-yl)-1-isopropylcyclopent-2-ene-1-carboxylic acid

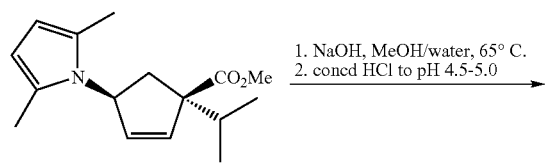

1. NaOH, MeOH/water, 65° C.
2. concd HCl to pH 4.5-5.0

The alkylated pyrrole methyl ester (1.38 kg, 5.197 mol) was dissolved in MeOH (7.7 L). DI water (2.5 L) was added followed by 10N NaOH (2.08 L, 20.786 mol). The batch was then heated to 65° C. for 16 h. The batch was cooled to 10° C. The product was crystallized by adjusting the pH to 4.5 with concd HCl. The slurry was aged for 1 h and DI water (15 L) was charged to the batch. The slurry was aged 18 h at 20-25° C. The solids were filtered, washed with 10% MeOH/DI water and dried in a vacuum oven (40-50° C., 25-26" Hg) to provide the alkylated pyrrole cyclopentene acid (1223 g, 95% yield).

EXAMPLE 4

3-(trifluoromethyl)-5,6,7,8-tetrahydro-1,6-naphthyridine

Step 1—N-[3-(Dimethylamino)-2-(trifluoromethyl)prop-2-enylidene]-N-methylmethanaminium hexafluorophosphate (CF$_3$DT)

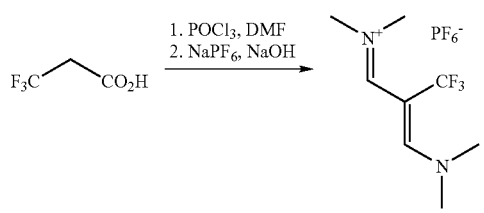

Phosphorous oxychloride (1.1 L, 11.8 mol) was added to dimethylformamide (2.6 L) at 4° C. over 1 h and the reaction mixture was allowed to warm to 20° C. 3,3,3-Trifluoropropionic acid (TFPA) (771 g, 6.02 mol) was added over 6 min. The reaction mixture was then aged at 50 to 60° C. for 4 h and then allowed to cool to room temperature. The TFPA/POCl$_3$/DMF reaction mixture was charged to a 5 L addition funnel. The reaction flask was rinsed with DMF, 3×75 mL, and the rinses also transferred to the 5 L addition funnel. Hexafluorophosphoric acid (980 mL, 60 wt % aqueous) was added to water (7.1 L) with cooling at 4° C. Sodium hydroxide (5 N, 2.0 L) was added slowly keeping the internal temperature below 15° C. The solution was then cooled to 0° C. Sodium hydroxide (5 N) was charged to a 2 L addition funnel and added concurrently with the TFPA/POCl$_3$/DMF reaction mixture at a rate such that the internal temperature remained below 5° C. and the pH varied from 3.05 to 3.6 (approx. 3.2 during most of the addition). The resulting yellow slurry was then aged for 60 min at ~0° C. The solids were filtered, slurry-washed with ice-cold water (2×4.0 L) then dried with a stream of N$_2$ under vacuum. A total of 1.785 kg (87%) of the CF3DT (vinamidinium salt) was obtained.

Step 2—N-(tert-Butoxycarbonyl)-3-(trifluoromethyl)-5,6,7,8-tetrahydro-1,6-naphthyridine

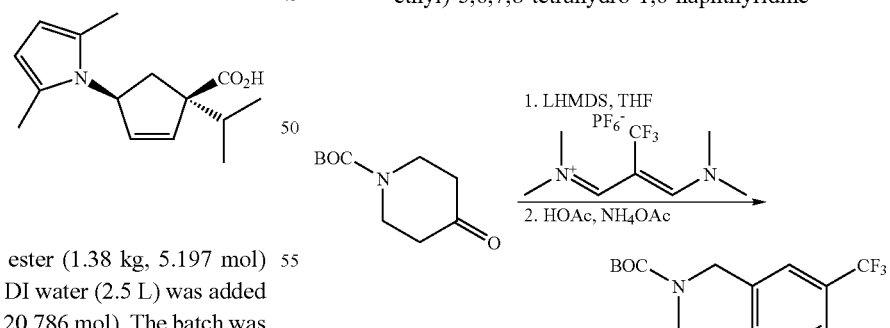

N-BOC-4-piperidone (672 g) in THF (2.72 L) was charged to a solution of lithium bis(trimethylsilyl) amide (LHMDS) (3.55 L, 1.0 M solution in THF) in THF (3.7 L) at −12° C. over 45 min. The reaction mixture was allowed to warm to room temperature. This mixture was added over 30 min to a slurry of CF$_3$DT (1.17 kg) in THF (5.45 L) cooled to −24° C. The reaction mixture was then aged for 2 h at ~−20° C. Acetic acid (295 mL) was added over 3 min. The reaction mixture was warmed to 20° C. over 1 h 15 min and ammonium acetate (741 g) was added in one portion. The reaction mixture was warmed to 64° C. and aged for 2 h at this temperature. The reaction mixture was cooled to room temperature then diluted with water (15.4 L) and methylcyclohexane (15.4 L). The mixture was agitated, the stirring stopped, and the layers were allowed to settle. The lower aqueous layer was removed and the organic layer was washed with 2 M aqueous citric acid (6.2 L). After agitation and separation of layers LC assay of the organic layer (total weight=19.8 kg) gave an assay yield of 617 g (64%) of the BOC naphthyridine.

Step 3—3-(trifluoromethyl)-5,6,7,8-tetrahydro-1,6-naphthyridine

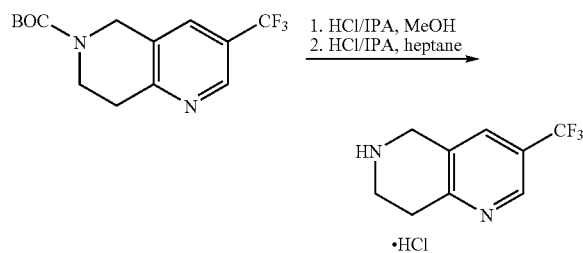

The organic layer from the naphthyridine formation containing N-(tert-butoxycarbonyl)-3-(trifluoromethyl)-5,6,7,8-tetrahydro-1,6-naphthyridine (34.2 kg total weight containing 989 g of BOC naphthyridine) was concentrated to an oil. The residue was diluted with methanol (6 L) and the solution was concentrated to an oil. Methanol (6 L) was added to the residue and this solution was concentrated to 2.3 L. The solution was diluted with methanol to a volume of 7.3 L and 4.58 M HCl in IPA (3.6 L) was added. The solution was heated to 55° C. and aged for 1 h. After cooling to room temperature water (5 L) was added. A solution of $K_2CO_3$ (2.28 kg) in water (5 L) was then carefully added (pH=10). The mixture was extracted with IPAc (3×10 L). The organic extractions contained 601 g (91%) of deprotected naphthyridine. The combined organic layers were concentrated and the residue was diluted with IPA (6 L) and reconcentrated. The resulting oil was diluted with EPA (6 L) and the solution was concentrated to a total volume of ~2 L. The solution was filtered through a sintered glass funnel, which was washed with EPA (3×1 L). The combined filtrate and rinses were concentrated to ~0.5 L and then diluted with IPA (1.95 L). The solution was heated to 60° C. and HCl in IPA (790 mL, 4.33 M by titration) was added over 40 min. During the addition the formation of solids became evident. Heptane (2.75 L) was added over 30 min after which heating was discontinued and the slurry was allowed to cool to room temperature overnight. Additional HCl/IPA (80 mL) and heptane (2×1.38 L) were added. The solids were filtered, washed with 2:1 heptane/IPA (3×550 mL), and dried under vacuum with a nitrogen stream to afford 678.8 g of 3-(trifluoromethyl)-5,6,7,8-tetrahydro-1,6-naphthyridine in 75% yield from BOC naphthyridine (497 g, 73.2 weight percent as free base).

EXAMPLE 5

(3R)-3-Methoxytetrahydro-4H-pyran-4-one

Step 1—tetrahyro-4H-pyran-4-one: A 22 L round-bottomed-flask equipped with a mechanical stirrer, thermocouple, and nitrogen inlet was charged with tetrahydro-4H-pyran-4-one (3.00 kg, 30.0 mol) and tripropylorthoformate (5.70 kg, 30.0 mol). The pump used for the transfer was flushed with chlorobenzene (300 mL) and the flush was added to the batch. The resulting solution was cooled in an ice bath to 5° C. Amberlyst-15 (60 g), previously washed with DI water then propanol and dried, was added in one portion. The mixture was stirred at ambient temperature for 16 h. This provides a solution of 2 (GC). The mixture was concentrated under vacuum (75 mm Hg). The solids were removed by filtration through a pad of solka floc and the filter pad was rinsed with MTBE (2 L). The filtrate was diluted with MTBE (26 L) and extracted with saturated aqueous $NaHCO_3$ (24 L) then water (2×16 L). The organic phase was concentrated under vacuum (500 mm Hg) to remove the MTBE. When the internal temperature reached 44° C., chlorobenzene (3 L) was added. The distillation was continued using a packed column at a rate that maintained a vapor temperature of about 85 to 90° C. Chlorobenzene was added periodically to maintain a constant volume. A total of 15 L was used. The batch temperature was maintained between 122 and 125° C. during the distillation. After 16 h, GC assay indicated >9:1 conversion. The vacuum was increased to 50 mm Hg and the reaction was distilled to provide a 53 wt % solution of 3 (3.13 kg, 73% yield) and chlorobenzene.

Step 2-3,4-dihydroxy-tetrahydro-2-H-pyran-4-sulfonic acid, sodium salt: A 50 L round-bottomed-flask equipped with a mechanical stirrer, nitrogen inlet and thermocouple was charged with acetone (12.7 L) and water (1.28 L). Hydroquinidine-1,4-phthalazinediyl diether ($DHQD_2PHAL$, 54.8 g, 0.070 mol), potassium osmate dihydrate (12.95 g, 0.035 mol), and 4-methylmorpholine N-oxide monohydrate (NMO, 1.078 kg, 7.74 mol) were added sequentially to the solvent and the resulting solution was cooled to 0° C. The propylenol ether (1.85 kg of a 54 wt % solution, 7.03 mol) was added over 7 h while maintaining a reaction temperature of about 0° C. A freshly prepared solution of $Na_2S_2O_5$ (802 g, 4.22 mol) and water (5.63 L) was added followed by glacial acetic acid (1.2 L). After aging 16 h at rt, the solids were removed by filtration and the filtrate was concentrated in vacuo to remove the acetone. Isopropanol (28 L) was added over 3.5 h to provide a colorless slurry. The solids were collected on a frit, rinsed with isopropanol (6 L) and dried in a vacuum oven to provide 958 g of 92 wt % (57% isolated yield) product that was 97.2% ee.

Step 3—4,4-dimethoxytetrahydro-2H-pyran-3-ol: A 22 L round bottomed flask equipped with a mechanical stirrer, 5 L dropping funnel, nitrogen inlet and thermocouple was charged with bisulfite adduct (893 g of a 92 wt % solid, 4.06 mol)MeOH (8.1 L) and trimethylorthoformate (948 g, 8.93 mol). The resulting slurry was warmed to 50° C. and a 1.89 M solution of HCl in MeOH (2.48 L, 4.69 mol) was added via dropping funnel over 40 min. The slurry was cooled to 7° C. and 50 wt % NaOH (340 mL) was added as a slow stream. The solids were collected on a frit and the filtrate was solvent switched to toluene using a total of 12 L toluene. The batch was concentrated to about 3 L then the solids were removed by filtration and the cake was rinsed with THF (2 L). A solution containing 577 g of product (3.56 mol in 5.33 L, 88% yield, 97.5% ee) results.

Step 4—(3R)-3-Methoxytetrahydro-4H-pyran-4-one: A 22 L round-bottomed-flask equipped with a thermocouple, nitrogen inlet and dropping funnel was charged with a solution of 6 (3.56 mol in 5.33 L) and THF (5.8 L). KF of the solution indicates 1.11 mol water is present. NaOt-Bu (494 g, 5.14 mol) was added in one portion to provide a clear yellow solution. The flask was immersed in an ice bath and $Me_2SO_4$ (737 g, 5.84 mol) was added over 20 min maintaining an internal temp of below 36° C. The cold bath was removed and the reaction mixture was aged for 4 h to provide a crude solution. Water (1.5 L) was added followed by 2N HCl (840 mL). The apparent pH of the two phase mixture was 0.6. After 20 h at RT, NaHCO$_3$ (497 g) was added and the mixture was extracted with IPAc (4×5 L). The combined organic phases were concentrated and the residual solids removed with a frit to provide a solution of the product (429 g in 2.635 kg of solution, d=0.914, 149 g/L, 93% yield, 97.2% ee).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. The compound:

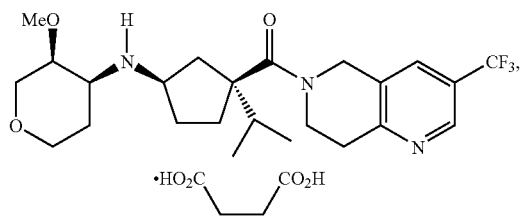

isolated as a crystalline solid.

2. A pharmaceutical composition which comprises an inert carrier and the compound of claim 1.

\* \* \* \* \*